(12) United States Patent
Brick et al.

(10) Patent No.: US 8,394,396 B2
(45) Date of Patent: Mar. 12, 2013

(54) METHOD OF MAKING INORGANIC POROUS PARTICLES

(75) Inventors: Mary Christine Brick, Webster, NY (US); Joseph Salvatore Sedita, Albion, NY (US); Joan Kay Williams, Rochester, NY (US); Mridula Nair, Penfield, NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 13/101,185

(22) Filed: May 5, 2011

(65) Prior Publication Data

US 2012/0282316 A1 Nov. 8, 2012

(51) Int. Cl.
 *A01N 25/26* (2006.01)
(52) U.S. Cl. ...................................... 424/421
(58) Field of Classification Search .................... 424/421
 See application file for complete search history.

(56) References Cited

U.S. PATENT DOCUMENTS

| 4,758,492 | A | 7/1988 | Nair | |
|---|---|---|---|---|
| 7,754,409 | B2 | 7/2010 | Nair et al. | |
| 2004/0151651 | A1* | 8/2004 | Navrotsky et al. | 423/335 |
| 2008/0176157 | A1 | 7/2008 | Nair et al. | |
| 2010/0021838 | A1 | 1/2010 | Putnam et al. | |

OTHER PUBLICATIONS

U.S. Appl. No. 13/101,78, filed May 5, 2011, titled "Inorganic Porous Particles with Stabilized Micropores" by M.C. Brick et al.
"Preparation of Silica Particles Encapsultating Retinol Using O/W/O Multiple Emulsions" by Myung-Han Lee et al, *J.Coll. Interface Sci.*, 240, 83-89 (2001).
"Synthesis of core-shell Hollow Silica Particles by Combining Multiple Emulsions and So-gel Techniques" by Ettiyappan P. et al., *Colloids and Surfaces A:Physiochem.Eng.Aspects* (2010).
"Stable microgel dispersions in isoparaffinic solvents from aqueous lattices" by M. Nair, *Progress in Organic Coatings*, 20 (1992) 53-61.

\* cited by examiner

*Primary Examiner* — Aradhana Sasan
(74) *Attorney, Agent, or Firm* — J. Lanny Tucker

(57) ABSTRACT

Sol-gel inorganic porous particles are composed of an inorganic compound that provides an inorganic solid phase including an external particle surface. They also have a first set of pores wherein the pores have an average diameter of less than 100 nm and a second set of pores wherein the pores have an average diameter of at least 100 nm, which second set of pores contains stabilizing organic microgel particles. These inorganic porous particles are prepared using a first oil phase comprising a first water-immiscible aprotic solvent having a dielectric constant of less than 10 and having dissolved therein organic microgel particles. An aqueous phase comprising a polar solvent, an inorganic gel precursor, a catalyst, and a dispersing surfactant is neutralized to initiate condensation of the inorganic gel precursor. An oil-in-water emulsion is then formed with the organic microgel particles in the first oil phase, which is dispersed as first oil phase droplets in the aqueous phase. A second oil phase is combined with the oil-in-water emulsion with the second oil phase to form an oil-in-water-in-oil emulsion comprising the first oil phase droplets in the aqueous phase.

22 Claims, No Drawings

METHOD OF MAKING INORGANIC POROUS PARTICLES

RELATED APPLICATION

Copending and commonly assigned U.S. Ser. No. 13/101,178 (filed on even date herewith by Brick, Sedita, and Nair, and entitled INORGANIC POROUS PARTICLES WITH STABILIZED MICROPORES, Attorney Docket 96788/JLT).

FIELD OF THE INVENTION

This invention relates to a method for preparing porous particles that have two sets of pores with different sizes and the larger pores are stabilized using organic microgel particles.

BACKGROUND OF THE INVENTION

Inorganic and organic porous particles have been prepared and used for decades for many different purposes. For example, porous particles have been described for use in chromatographic columns, ion exchange and adsorption resins, drug delivery devices, cosmetic formulations, papers, and paints. The methods for generating pores in organic and inorganic particles are well known in the field of polymer science. However, each type of porous particle often requires unique methods for its manufacture. Some methods of manufacture produce large particles without any control of the pore size while other manufacturing methods control the pore size without controlling the overall particle size According the International Union of Pure and Applied Chemistry (IUPAC, www.iupac.org), micropores, mesopores, and macropores refer to pores with diameters of below 2 nm, from 2 to 50 nm, and above 50 nm, respectively.

Many applications use inorganic materials containing both mesopores and macropores. Inorganic porous materials generally exhibit advantages of higher mechanical strength, higher thermal stability, and higher chemical durability than those derived from organic polymers. These features meet the demands of a high temperature and high pressure operation of separation or reaction processes favored in a large scale production. The sol gel process is commonly used to prepare inorganic porous materials because of its ability to form inorganic networks from silicon or other metal alkoxides with desirable hardness, optical transparency, chemical durability, tailored porosity, and thermal resistance using a room temperature process. Products made from sol-gel technology include optics, protective and porous films, optical coatings, window insulators, dielectric and electronic coatings, high temperature superconductors, reinforcement fibers, fillers, and catalysts. Many uses exist for inorganic materials with mesopores and macropores prepared from the sol-gel process. Examples include inorganic films and membranes for microfiltration and ultrafiltration of beverage and drinking water purification and wastewater treatment, porous structures as catalysts and enzyme supports, and porous monolith chromatography columns as separating media for liquid and gas mixtures. Monolithic macroporous silica with appropriate mesopores has proved to be an efficient separation medium in liquid chromatography. A monolith is a continuous piece of highly porous material usually created by in situ polymerization of a monomeric solution and characterized by a defined pore structure consisting of large flow-through macropores for high permeability and small diffusion mesopores for desired surface area providing high loadability.

While the macroporous structure is formed through concurrent phase separation and gelation in the course of hydrolysis and polycondensation of alkoxysilanes in the presence of organic additives, the mesopore structure is tailored by post gelation treatments such as solvent-exchange and accelerating the rate of condensation.

While inorganic monoliths, films, and coatings with a double-pore structure prepared from the sol-gel process are common, inorganic particles with this double-pore structure are less common, because of the difficulty in maintaining the internal macropore structure due to collapse of the pores from the resulting high stresses occurring within the particle during drying. Useful porous inorganic microspheres have been prepared using sol-gel reactions and used as "microreactors" to deliver controlled release of cosmetics, vitamins, or reactive chemicals. Such inorganic porous particles have been prepared using oil-in-water-in-oil emulsions. See for example Lee et al., *J. Coll. Interface Sci.* 240, 83-89, 2001, in which retinol is entrapped within the macropores of the inorganic porous particles. These particles essentially have one set of mesopores pores, derived from the porous matrix. The larger macropores formed from the first emulsion are completely filled with material preventing collapse during drying. Ettiyappan, P. et al., *Colloids and Surfaces A: Physicochem. Eng. Aspects*, August 2010 disclose inorganic particles formed using a single water-in-oil emulsion process that inverts to form an oil-in-water-in oil sol-gel multiple emulsion where the first inner oil-in-water emulsion is destabilized to form hollow particles.

It is also known to include marker materials in organic porous particles so that the particles can be detected for a specific purpose. For example, U.S. Patent Applications 2008/0176157 (Nair et al.) and 2010/0021838 (Putnam et al.) and U.S. Pat. No. 7,754,409 (Nair et al.) describe organic porous particles and a method for their manufacture, which organic porous particles are designed to be toner particles for use in electrophotography. Such organic porous particles can contain a colorant such as carbon black or another pigment to provide desired black-and-white or color electrophotographic images. The organic porous particles can be prepared using a multiple emulsion process in combination with a suspension process (such as "evaporative limited coalescence", ELC) in a reproducible manner and with a narrow particle size distribution.

While various organic porous particles have been prepared for such uses, it is very difficult to prepare inorganic porous particles with two sets of pores with different sizes using an oil-in-water-in-oil sol-gel multiple emulsion processes, due to the high capillary pressures during drying of the sol-gel matrix that result in shrinkage and collapse of pores. In some cases the dry particles have little or no pores greater than 100 nm in diameter.

There exists a need for a method of preparing inorganic porous particles with two sets of pore sizes in which the pores are essentially empty to act as a scaffold for addition or adsorption of useful materials. Thus, there is a need to stabilize the internal macropores in inorganic porous particles prepared by an oil-in-water-in-oil sol-gel multiple emulsion process to maintain the internal integrity of the inner emulsion and macropores during particle formation and drying.

SUMMARY OF THE INVENTION

The present invention provides a method of preparing an inorganic porous particle comprising an inorganic compound that provides an inorganic solid phase including an external particle surface, and further comprising a first set of pores wherein the pores have an average diameter of less than 100 nm and a second set of pores wherein the pores have an average diameter of at least 100 nm, which second set of pores comprise stabilizing organic microgel particles, and the first and second sets of pores are isolated from each other in the inorganic solid phase, the method comprising:

providing a first oil phase comprising a first water-immiscible aprotic solvent having a dielectric constant of less than 10 and having dissolved therein organic microgel particles, providing an aqueous phase comprising a polar solvent, an inorganic gel precursor, a catalyst, and a dispersing surfactant, neutralizing the aqueous phase to initiate condensation of the inorganic gel precursor, providing an oil-in-water emulsion that comprises the organic microgel particles in the first oil phase, which is dispersed as first oil phase droplets in the aqueous phase, providing a second oil phase comprising a second water-immiscible aprotic solvent having a dielectric constant of less than 10 and a dispersing surfactant, combining the oil-in-water emulsion with the second oil phase to form an oil-in-water-in-oil emulsion comprising the first oil phase droplets in the aqueous phase, which is dispersed as aqueous phase droplets in the second oil phase, condensing the inorganic gel precursor in the aqueous phase droplets, and forming precursor inorganic porous particles containing a first set of pores wherein the pores have an average diameter of less than 100 nm and a second set of pores wherein the pores have an average diameter of at least 100 nm.

The inorganic porous particles prepared using the method of this invention comprise two different sets of pores of different average diameters. The smaller pores are formed by the condensation reactions in the sol-gel matrix of the aqueous phase, and the larger pores are formed from voids caused by the aqueous phase sol-gel matrix that has condensed around the first oil phase droplets. The larger pores are stabilized by the presence of stabilizing organic microgel particles in the first oil phase that prevent the collapse of the inorganic matrix around the large pores during the drying process. The organic microgel particles are prepared from a particular mixture of ethylenically unsaturated polymerizable monomers, at least one of which has crosslinkable groups. These organic microgel particles are included in the first oil phase used in the method of making the porous particles so that the organic microgel particles are incorporated into the larger pores. In most instances, the amount of stabilizing organic microgel particles is low enough so that most of the pore volume is empty.

DETAILED DESCRIPTION OF THE INVENTION

The inorganic porous particles prepared using this invention can have various uses including but not limited to use in, optics, drinking water purification, wastewater treatment, chromatographic columns, ion exchange and adsorption resins, drug delivery devices, cosmetic formulations, pharmaceuticals, vitamins, papers, fabrics, fibers, paints, inks, adhesives, electrophotographic toners, security systems for detection of counterfeits, document authentication, and labeling of consumer goods (such as designer clothes, handbags, perfumes, and cosmetics). They can also be used in paper and plastic cards, for example driver's licenses, passports, and other identification cards. Moreover, the inorganic porous particles can be incorporated into packaging and packaging components such as labels, tape, staples, foils, paperboard, and cardboard packing. The inorganic porous particles can also be included in varnishes (colored or colorless) and other coating compositions, polymeric films and fibers, and formed polymer, glass, and ceramic articles including ceramic substrates, bottles, and bottle caps.

The inorganic porous particles are generally prepared, as described below, using multiple oil phases and an aqueous phase.

Unless otherwise indicated, the terms "inorganic porous particle", "inorganic porous particles", and "particles" are used herein, unless otherwise indicated, to refer to materials of the present invention. The inorganic porous particles comprise a inorganic solid (polymer) phase having an external particle surface and at least two sets of discrete pores (at least first and second different discrete types of pores as defined below) dispersed within the solid phase.

In many embodiments, the inorganic solid phase of the inorganic porous particles has the same composition. That is, the inorganic solid phase is uniform in composition including any additives that may be incorporated into the inorganic solid phase materials. In addition, if mixtures of inorganic materials are used in the solid phase, those mixtures are dispersed uniformly throughout.

The term "porogen" refers to a pore forming agent used to make the inorganic porous particles. In this invention, the porogen can be the first oil phase of the oil-in-water emulsion and the pore stabilizing organic microgel particles, and any other additive in the aqueous phase that can modulate the size of the large pores in the porous particles.

As used in this disclosure, the term "isolated from each other" refers to the pores of the two sets of pores being different and separate from each other (distinct) pores.

Each set of pores includes a plurality of pores, which pores are isolated from each other, and the pores of each set of pores are isolated from all other pores of the other sets of pores in the inorganic porous particle. One or both sets of pores can contain a bioactive material, marker material, or reactive chemical material, and the second set of pores can be empty or contain a different bioactive material, marker material, or reactive chemical material.

One set (first set) of pores contains pores having an average diameter of up to but not 100 nm, and typically having an average diameter of at least 1 nm and up to and including 50 nm. Another set (second set) of pores contains pores having an average diameter of at least 100 nm, and typically having an average diameter of at least 100 nm and up to and including 10,000 nm or up to and including 5,000 nm. The porous particles generally include closed pores of the noted sizes and shapes (pores entirely within the solid phase). While there may be open pores on the surface of the inorganic porous particle, such open pores are not desirable and are generally present only by accident. The size of the inorganic porous particles, the materials used in their formulation, and the manufacturing conditions are the primary controlling factors for pore size. For spherical pores, the average size is an "average diameter". For non-spherical pores, the average size refers to the "average largest dimension". The size distribution of the small pores can be determined by using nitrogen gas adsorption and desorption isotherms and applying the Kelvin equation in the manner of the Barrett, Joyner, and Halenda algorithm (E. P. Barrett, L. G. Joyner and P. H. Halenda, J. Amer. Chem. Soc. 73, 373, 1951), assuming a cylindrical pore model equal to 4× pore volume/surface area. The size distribution of the large pores can be determined by analyzing Scanning Electron Microscopy (SEM) images of fractured inorganic porous particles using a commercial statistical analysis software package to study the distribution of the pores within the porous particles, or by manually measuring the pore diameters using the scale in the SEM images. For example, the "average" pore size can be determined by calculating the average diameter of 20 measured pores.

The inorganic porous particles generally have an average diameter at least 1 μm and up to and including 100 μm, or typically at least 5 μm and up to an including 80 μm, with this average size being measured by automated image analysis and flow cytometry using any suitable equipment designed for this purpose. The average size refers to the diameter for spherical inorganic porous particles and the largest diameter for the non-spherical porous particles. In general, the inorganic porous particles have porosity of at least 10% and up to and including 70%, or more likely at least 10% and up to and including 50%, or typically at least 10% and up to an including 40%, all based on the total inorganic porous particle volume. Porosity can be measured by the mercury intrusion technique.

For example, in some embodiments, the pores in the first set of pores in the inorganic porous particle have an average diameter of at least 1 nm but less than 100 nm and the pores in the second set of pores of the porous particle have an average diameter at least 100 nm and up to and including 10,000 nm, and the inorganic porous particle has an average diameter of at least 1 μm and up to and including 100 μm.

The pores of the second set of pores (larger pores) are at least partially filled with stabilizing organic microgel particles (described below) in an amount of generally at least 1% and up to and including 20% of the volume of these pores, or typically up to and including 10% of the pore volume. These organic microgel particles and their preparation are described in U.S. Pat. No. 4,758,492 (Nair) that is incorporated herein by reference for the information relating to the organic microgel particles.

Such stabilizing organic microgel particles can comprise a copolymer that comprises randomly recurring units from each of a) and b) below:
  a) recurring units derived from crosslinkable ethylenically unsaturated polymerizable monomers, and
  b) recurring units derived from one or more of:
    i) an ethylenically unsaturated polymerizable monomer, the homopolymer of which would be insoluble in but swellable by an isoparaffinic hydrocarbon liquid,
    ii) an ethylenically unsaturated polymerizable monomer, the homopolymer of which would be soluble in the isoparaffinic hydrocarbon liquid, and
    iii) an ethylenically unsaturated polymerizable monomer, the homopolymer of which would be insoluble in and not swellable by the isoparaffinic hydrocarbon liquid.

For example, each stabilizing organic microgel particle can comprise recurring units derived from a mixture of ethylenically unsaturated polymerizable monomers, wherein at least 0.5 weight % and up to and including 15 weight % of the mixture of monomers comprises a) monomers, and the remainder of the mixture of monomers comprises b) monomers. More likely, amount of the a) monomers in the mixture of ethylenically unsaturated polymerizable monomers is at least 0.5 weight % and up to and including 7 weight %.

In some embodiments, the mixture of ethylenically unsaturated polymerizable monomers used to prepare the stabilizing organic microgel particles includes at least 0.5 weight % and up to and including 15 weight % of the a) monomers, from 0 weight % and up to and including 99.5 weight % of the b)i) monomers, from 0 weight % and up to and including 98.5 weight % of the b)ii) monomers, and from 0 weight % and up to and including 60 weight % of the b)iii) monomers, provided that:

if there is more than 0 weight % of the b)iii) monomers in the mixture of monomers, then there is more than 0 weight % of the b)ii) monomers;

if there is more than 9 weight % of the b)iii) monomers in the mixture of monomers, then there less than 10 weight % of the a) monomers; and all of the monomers are present such that the copolymer would be insoluble in the isoparaffinic hydrocarbon liquid but would be swellable in that liquid. When the surface of the microgel particle is weakly acidic, the microgel particles are characterized in that an aqueous latex of the microgel particles (40 g per liter of water), after formation by latex emulsion polymerization and removal of any surfactant present during the polymerization, would exhibit a pH greater than 3 at 25° C. and in that the pKa of any acidic moiety bonded to the surface of each microgel particle is at least 4.

Still other organic microgel particles can be prepared from a mixture of ethylenically unsaturated polymerizable monomers in which at least 0.5 weight % and up to and including 7 weight % of the mixture comprises a) monomers, from 0 weight % and up to and including 10 weight % of the mixtures comprises b)i) monomers, at least 25 weight % and up to and including 60 weight % of the mixture comprises b)ii) monomers, and at least 30 weight % and up to and including 60 weight % of the mixture comprises b)iii) monomers.

In still other embodiments, the monomer mixture comprises at least 0.5 weight % and up to and including 7 weight % of the a) monomers, at least 48 weight % and up to and including 93 weight % of the b)i) monomers, at least 5 weight % and up to and including 50 weight % of the b)ii) monomers, and from 0 weight % and up to and including 9 weight % of the b)iii) monomers.

In other embodiments, the monomer mixture comprises at least 2 weight % and up to and including 5 weight % of the a) monomers, at least 58 weight % and up to and including 90 weight % of the b)i) monomers, at least 8 weight % and up to and including 40 weight % of the b)ii) monomers, and from 0 weight % and up to and including 9 weight % of the b)iii) monomers.

There are many useful monomers that can be included in the various groups of monomers described above, and a skilled polymeric chemist would be able to appropriately choose useful combinations of monomers. However, to aid that skilled worker, representative polyfunctional monomers in the a) group of monomers include but are not limited to, divinyl benzene, ethylene glycol dimethacrylate, ethylene glycol diacrylate, tetra(ethylene glycol)diacrylate, di(ethylene glycol)dimethacrylate, tri(ethylene glycol)dimethacrylate, N,N'-methylenebis(methacrylamide), and N,N'(1,2-dihydroxyethylene)bisacrylamide.

Useful b)i) monomers include but are not limited to, alkyl (meth)acrylates (having 4 to 7 carbon atoms in the alkyl groups), vinyl alkanecarboxylates (having 4 to 7 carbon atoms in the alkane groups), substituted or unsubstituted styrenes optionally having one or more alkyl (1-3 carbon) substituents. Examples of useful b)i) monomers include isobutyl methacrylate, isobutyl acrylate, ethyl methacrylate, p-t-butyl styrene, methylstyrene, t-butyl acrylate, t-butyl methacrylate, and n-butyl methacrylate.

Useful b)ii) monomers include but are not limited to, alkyl (meth)acrylates (having at least carbon atoms in the linear or cyclic alkyl groups), vinyl alkanecarboxylates (having at least 8 carbon atoms in the alkane groups), substituted or unsubstituted styrenes optionally having one or more alkyl (at least 4 carbon atoms) substituents, and olefinic hydrocarbons. Examples of useful b)ii) monomers include 2-ethyl hexyl methacrylate, 2-ethylhexyl acrylate, lauryl acrylate, lauryl methacrylate, 4-t-butylstyrene, isoprene, and 1,3-butadiene.

Useful b)iii) monomers include but are not limited to, styrene and styrene substituted with one or more electronegative substituents, alkyl (meth)acrylates (up to 4 carbon atoms in the alkyl group), vinyl alkane carboxylates (having 4 or less carbon atoms in the alkane groups), nitriles, acrylic and styrene monomers having hydroxy, amido, amino, or quaternary ammonium substituents, alkyl acrylamides and alkyl methacrylamides. Examples of useful b)iii) monomers include methacrylic acid, acrylic acid, N-[2-(methacryloyloxy)ethyl]-N,N,N-trimethylammonium methosulfate, N-vinyl-2-pyrrolidone, and 2-hydroxyethyl acrylate.

Other specific useful monomers for all of these categories are described in U.S. Pat. No. 4,758,492 (noted above).

In the definitions of these microgel particles, unless otherwise stated, the term "soluble", "insoluble", "swellable", and "pKa" are interpreted as follows. A material is soluble in a medium if a single homogeneous phase is formed when the material is mixed with an excess amount of the medium at 25° C. A material is insoluble in a medium if a single homogeneous phase is not formed when the material is mixed with an excess amount of the medium at 25° C. A polymeric material is swellable by a medium if, when mixed with an excess of the medium at 25° C., the polymeric material absorbs enough of the medium such that the glass transition temperature (Tg) of the polymeric material plus absorbed medium is at least 10° C. lower than the Tg of the polymeric material itself. The Tg is determined using any methods well known in the art. The term "pKa" is used in accordance with commonly accepted meaning.

In many embodiments, each stabilizing organic microgel particle has a weakly acidic outer surface. The term "weakly acidic" means that the surface can have moieties that have a pKa greater than 3 and this feature can be provided by using an appropriate amount of ethylenically unsaturated polymerizable monomers that have acidic moieties such as carboxylic acid groups that can be on the particles surfaces.

The organic microgel particles can be prepared using aqueous emulsion polymerization techniques wherein the monomers are dispersed in an aqueous phase with emulsifying agents and free radical initiators. The weakly acidic particle surface can also be provided using weakly acidic initiators alone, or in combination with acidic monomers. Methods for yield relatively monodisperse particle size distributions can also be used to prepare the organic microgel particles. Further details for making these organic microgel particles are provides in U.S. Pat. No. 4,758,492 (noted above).

Each stabilizing organic microgel particle has a diameter measured in a non-swollen state of at least 0.02 µm and up to and including 1 µm, and typically of at least 0.05 µm and up to and including 0.5 µm.

The stabilizing organic microgel particles are generally present in the inorganic porous particles in an amount of at least 0.5 weight %, or typically in an amount of at least 0.5 weight % and up to and including 10 weight %.

The inorganic porous particles can be spherical or non-spherical depending upon the desired use. The shape of the inorganic porous particles can be characterized by an "aspect ratio" that is defined as the ratio of the largest perpendicular length to the longest length. These lengths can be determined for example by optical measurements using a commercial particle shape analyzer such as the Sysmex FPIA-3000 (Malvern Instruments). For example, inorganic porous particles that are considered "spherical" for this invention can have an aspect ratio of at least 0.95 and up to and including 1. For the non-spherical inorganic porous particles of this invention, the aspect ratio can be as low as 0.1 and up to and including 0.95, and in some embodiments, the aspect ratio can be 0.95 and down to and including 0.4.

The inorganic porous particles prepared using this invention can have one or more marker materials located in either or both sets of pores, but in many embodiments, both sets of pores are empty of marker materials, but can include one or more pigments, chemicals, or pharmaceuticals. In some embodiments, at least some marker materials are located in at least some of either or both sets of pores.

Useful marker materials can be colored dyes or pigments (or colorants) or metallic pigments. Such colorants can include but are not limited to, those described in U.S. Reissue Pat. 31,072 (Jadwin et al.) and in U.S. Pat. Nos. 4,160,644 (Ryan), and 4,416,965 (Sandhu et al.), 4,414,152 (Santilli et al.). Other useful colorants are described in U.S. Pat. No. 5,385,803 (Duff et al.) and EP 2,025,525 (Wosnick et al.) that are incorporated herein by reference. For example, a carbon black can be present in the inorganic porous particles, for example in at least some of the pores of either or both sets of pores.

Other classes of marker materials include but are not limited to, fluorescing materials, radioisotopes, particles of metals and metal-containing compounds (such as metal oxides, metal sulfides, and metal oxyhydroxides) having magnetic moments, luminescing compounds, as well as bioactive materials. Certain reactive chemicals can be used as markers and kept separate in discrete pores until their reaction is needed. Examples of such reactive chemicals include acids and bases, and isocyanates and amines, epoxies, carboxylic acids, hydroxyl compounds, silanes, silica, alumina and other such sols.

When present, the various marker materials can be present, independently, in an amount of up to and including 35 weight %, or at least 0.001 and up to and including 25 weight %, all based on total particle weight.

Alternatively, the inorganic porous particle can comprise a pharmaceutical agent, biocide, chemical catalyst, dispersant, colorant, block or graft copolymer, metal oxide particles, organic or inorganic filler particles, or bioactive material in at least some pores.

The inorganic porous particles or mixtures of a multiplicity of inorganic porous particles can be provided as powders, or dispersed in liquid suspensions such as suspensions in organic solvents such as alcohols, esters, ketones, hydrocarbons, nitriles, and ethers, or as suspensions in water. Such suspensions can also include surfactants or suspending agents to keep the inorganic porous particles suspended.

The other compositional features of the inorganic porous particles are described in the following description of the desired method for preparing the porous particles. The inorganic compounds providing the inorganic solid phase are described below.

The inorganic porous particles prepared using this invention are prepared by a sol-gel based process in which alkoxides of suitable elements (including transition metals, and silicon) are hydrolyzed and condensed to form a sol. The latter is further condensed to form a gel network.

The inorganic porous particles are generally prepared, as described below, using multiple oil phases and an aqueous phase. This method comprises: providing a first oil phase comprising a first water-immiscible aprotic solvent having a dielectric constant of less than 10 and having dissolved therein organic microgel particles, providing an aqueous phase comprising a polar solvent, an inorganic gel precursor, a dispersing surfactant, and a catalyst for hydrolyzing and initiating the condensation of the inorganic gel precursor, neutralizing the aqueous phase to initiate condensation of the inorganic gel precursor, providing a first oil-in-water emulsion that comprises the organic microgel particles in the first oil phase, which is dispersed as first oil phase droplets in the aqueous phase, providing a second oil phase comprising a second water-immiscible aprotic solvent having a dielectric constant of less than 10 and a dispersing surfactant, combining the oil-in-water emulsion with the second oil phase to form an oil-in-water-in-oil emulsion comprising the first oil phase droplets in the aqueous phase, which is dispersed as aqueous phase droplets in the second oil phase, condensing the inorganic gel precursor in the aqueous phase droplets, and forming precursor inorganic porous particles containing a first set of pores wherein the pores have an average diameter less than 100 nm and a second set of pores wherein the pores have an average diameter of at least 100 nm.

The process can include steps of separating (isolating) the inorganic porous particles by removing the solution that typically comprises solvent(s) and other materials (such as surfactants) from the precursor inorganic porous particles. The step of separating can be accomplished by known techniques such as filtering or decanting off the solvents and surfactants.

The removal of any remaining solution can be carried out by rinsing or washing of the precursor inorganic porous particles with a suitable solvent or combination of solvents, followed by the removal of any remaining solvent from the inorganic porous particles from the second oil phase. This can be accomplished by known techniques such as by evaporating or drying to yield porous inorganic porous particles containing a first set of pores having an average diameter less than 100 nm and a second set of pores having an average diameter of at least 100 nm.

Drying can be carried out at ambient temperature and pressure, or under vacuum or by freeze drying. Examples of drying processes are described in ACS Symposium 520, Polymeric delivery systems, properties and applications, I. C. Jacobs and N. S. Mason, Chapter 1, Polymer Delivery Systems Concepts, pp. 1-17, 1993, the contents of which are incorporated herein by reference.

The inorganic porous particles can be prepared as described above using a multi-step process that firstly comprises providing a first oil phase comprising a first water-immiscible aprotic solvent having a dielectric constant of less than 10 and having dissolved therein the organic microgel particles described above. These organic microgel particles are generally present in the first oil phase in an amount of at least 1 weight % and up to and including 20 weight %, or more likely at least 2 weight % and up to and including 10 weight % based on the total first oil phase weight.

Useful water-immiscible aprotic solvents having a dielectric constant of less than 10 include can be selected from aliphatic and aromatic hydrocarbons, and a mixture of two or more of these aprotic solvents. Examples of such aliphatic and aromatic hydrocarbons include but are not limited to, toluene, xylene, cyclohexane, decane, dodecane, hexane, heptanes, pentane, ethyl acetate, propyl acetate, mineral oil, and kerosene. Cyclohexane is particularly useful.

The first oil phase can further comprise an organic polymeric dispersant to improve the efficacy of the organic microgel particles as a stabilizer for the first oil-in-water droplets. Such dispersants are more soluble in the first oil phase than in the aqueous phase and include but are not limited to, compounds comprising at least two different segments. One segment comprises heteroatoms for adsorption to the microgel particles and a second segment comprises moieties that are soluble in the oil phase. For example, the first segment can comprise amine groups for attachment and the second segment can comprise long hydrocarbon moieties, for compatibility with the oil phase. Such compounds can be obtained commercially under the tradenames OLOA™ polyethyleneimine substituted succinimide derivative of polyisobutylene, and Solsperse® 13940, (polyesteramine aziridine-hydroxy stearic acid copolymer), and poly(t-butyl styrene-co-lithium methacrylate). Such dispersants can be present in the first oil phase in an amount of at least 0.1 weight % and up to and including 20 weight % based on the total first oil phase weight.

In addition to the first oil phase, an aqueous phase is provided to make the inorganic porous particles. This aqueous phase comprises, in water, one or more polar solvents that are generally water-miscible organic solvents. Because water and alkoxides are immiscible, a mutual solvent such as a water-miscible organic solvent that is also miscible with the alkoxide is utilized to facilitate the hydrolysis of the alkoxide in water. For example, the polar solvent can be selected from the group consisting of water-miscible alcohols having 1 to 8 carbon atoms. Representative polar solvents include but are not limited to, methanol, isopropanol, ethanol, n-butanol, n-hexanol, n-propanol, and isopropanol. Such one or more polar solvents are generally provided in an amount of at least 1 weight % and up to and including 50 weight % of the total aqueous phase weight.

In addition, the aqueous phase comprises one or more inorganic gel precursors, including but not limited to, a substituted or unsubstituted alkoxide, such as substituted alkoxides having one or more alkyl, aryl, aminoalkyl, aminoaryl, glycidoxyalkyl, or glycidoxyaryl substituents, or mixtures thereof. Typically, the silica gel precursor is a silicon alkoxide or a silicon alkyl alkoxide. The gel precursor can be an oxide gel precursor including silicon oxide gel precursor, or a transition metal oxide precursor. The identity of the gel precursor chosen that is, whether a silicon oxide gel precursor or a particular metal oxide gel precursor chosen for use in a process, will depend on the intended use of the porous particles and, in particular, the suitability of the final product resulting from the condensation of the gel precursor for the intended use of the porous particles. The gel precursor is typically a silica-based gel precursor, an alumina-based gel precursor, a titanium dioxide-based gel precursor, an iron oxide based gel precursor, a zirconium dioxide-based gel precursor, or any combination thereof. A functionalized, derivatized or partially hydrolysed gel precursor can be used.

For silica, there is a long list of potential silicon precursors that for convenience can be divided into 4 categories: silicates (silicon acetate, silicic acid, and salts thereof), silsequioxanes and poly-silsequioxanes, silicon alkoxides (from silicon methoxide (C1) to silicon octadecyloxide (C18)), and functionalized alkoxides (such as ethyltrimethoxysilane, aminopropyltriethoxysilane, vinyltrimethoxysilane, diethyldiethoxysilane, and diphenyldiethoxysilane). Further specific examples of silica-based gel precursors include tetramethoxysilane (TMOS), tetraethoxysilane (TEOS), tetrabutoxysilane (TBOS), tetrapropoxysilane (TPOS), polydiethoxysilane, methyltrimethoxysilane, methyltriethoxysilane, ethyltriethoxysilane, octylpolysilsesquioxane, and hexylpolysilsesquioxane-.

Examples of alumina-based gel precursors include aluminum ethoxide, aluminum n- or iso-propoxide, and aluminum n- or sec- or tert-butoxide. The alkoxide can also be modified using carboxylic acids (acetic, methacrylic, and 2-ethylhexanoic) or beta di-ketones such as acetylacetone, ethyl-acetylacetone, benzoylacetone, and other complexing agents.

Examples of titanium or zirconium gel precursors include alkoxides (such as ethoxide, propoxide, and butoxide), metal salts (such as chloride, oxychloride, sulfate, and nitrate), and acid and beta diketone complexes.

The silica gel precursor or the metal oxide gel precursor can include from one to four alkoxide groups each having 1 or more oxygen atoms and 1 to 18 carbon atoms, more typically 1 to 5 carbon atoms. The alkoxide groups can be replaced by one or more suitable modifying groups or functionalized or derivatised by one or more suitable derivatizing groups (see K. Tsuru et al., *J. Material Sci. Mater. Medicine*, 1997, 8, which is incorporated herein by reference).

Typically, the silica gel precursor is a silicon alkoxide or a silicon alkyl alkoxide.

Particular examples of suitable silicon alkoxide precursors include but are not limited to, methoxide, ethoxide, iso-propoxide, butoxide, and pentyl oxide. Particular examples of suitable silicon or metal alkyl (or phenyl) alkoxide precursors include but are not limited to, methyl trimethoxysilane, dimethyldimethoxysilane, ethyltriethoxysilane, diethyldiethoxysilane, triethyl-methoxysilane, phenyltriethoxysilane, diphenyldiethoxysilane, and vinyltriethoxysilane. Alternatively, the silica gel precursor can be a silicon carboxylate such as an acetate, tartrate, oxalate, lactate, propylate, formate, or citrate. Examples of other functional groups attached to silica gel precursors include esters, alkylamines, and amides.

Typically, the metal oxide gel precursor is a metal alkoxide that can be derivatised or functionalized. Typically, the transition metal oxide gel precursor is a transition metal alkoxide and the lanthanide metal oxide gel precursor is a lanthanide metal alkoxide. Examples of suitable metal oxide precursors include alkoxides such as methoxide, ethoxide, iso-propoxide, butyloxide, and pentyl oxide. Alternatively, the metal oxide gel precursor can be a metal carboxylate or a metal beta-diketonate, for example, an acetate, tartrate, oxalate, lactate, propylate, formate, citrate, or acetylacetonate. Examples of other functional groups attached to metal oxide precursors include esters, alkylamines, and amides. More than one type of metal ion or lanthanide ion can be present.

Particularly useful inorganic gel precursors are tetramethoxysilane and tetraethoxysilane. These compounds eventually form the inorganic metal oxide network forming the solid phase of the inorganic porous particles, which inorganic metal oxide network can be selected from alumina, silica, titania, zirconia, an organically-substituted metal oxide, and mixtures thereof. A particularly desirable inorganic oxide network comprises silica. The inorganic gel precursors are present in the aqueous phase in an amount of at least 10 weight % and up to and including 70 weight %, and typically in an amount of at least 40 weight % and up to and including 60 weight %, based on the total aqueous phase weight. Mixtures of inorganic gel precursors can be used if desired to provide an inorganic metal oxide network comprises two or more different metal oxides.

Although hydrolysis of the metal alkoxide can occur without addition of an external catalyst, it is most rapid and complete when one is used. Therefore, an external catalyst can be present in the aqueous phase to increase the hydrolysis rate of the metal alkoxide precursor. The hydrolysis rate increases linearly with the concentration of $H^+$ or $H_3O^+$ ions in acidic media and with the concentration of $OH^-$ ion in basic medium.

Such catalysts are chosen based on the pH and ionic strength of the solution in which the hydrolysis and condensation can occur, which varies over a wide range, depending on the nature of the active material. However, the rate of hydrolysis and the rate condensation can vary according to the metal oxide precursor. Generally, the pH used in the hydrolysis and condensation process can range from 0 and up to and including 14, and is typically at least 1 and up to and including 11. When an acidic catalyst is used, the pH range is typically at least 1 and up to and including 6.5, or at least 1 and up to and including 4.5. When a basic catalyst is used, the pH range is typically at least 7 and up to and including 14 or at least 7 and up to and including 11. The pH at which the polycondensation (or condensation) is carried out is normally chosen so as to be at a value or within a certain pH range that does not substantially affect the activity of the active materials (which will depend on the nature of the active materials or the stability of the surfactant). One of ordinary skill in the art can determine optimal pH and ionic strength for particular gel precursors/active material combinations using the methods described herein. Useful catalysts in the aqueous phase are inorganic and organic acids or inorganic or organic bases, and include but are not limited to, hydrochloric acid, acetic acid, sodium hydroxide, potassium hydroxide, ammonium hydroxide, lower alkylamines, potassium fluoride, and hydrogen fluoride. Mixtures of catalysts can also be used if desired, particularly if different inorganic gel precursors are used that require different catalysts for solid network formation.

It is also useful to include one or more dispersing surfactants in the aqueous phase in an amount of at least 0.1 weight % and up to and including 50 weight %, based on the total aqueous phase weight. Such dispersing surfactants can be hydrophilic surfactants including but not limited to, alcohols, alkanolamides, alkanolamines, alkylaryl sulfonates, alkylaryl sulfonic acids, alkylbenzenes, amine acetates, amine oxides, amines and amides, sulfonates, amines and amides, betaine derivatives, block copolymers, carboxylated alcohol or alkylphenol ethoxylates, carboxylic acids, fatty acids, diphenyl sulfonate derivatives, ethoxylated alcohols, ethoxylated alkylphenols, ethoxylated amines, ethoxylated amides, ethoxylated aryl phenols, ethoxylated fatty acids, ethoxylated fatty esters and oils, fatty esters, glycerol esters, glycol esters, imidazoles and imidazoline derivatives, isothionates, lanolin-based derivatives, lecithin and lecithin derivatives, methyl esters, monoglycerides and derivatives, olefin sulfonates, phosphate esters, phosphorous organic derivatives, polyethylene glycols, polymeric polysaccharides, acrylic acids, acrylamides and vinyl alcohols, propoxylated and ethoxylated fatty acids, alcohols and alkyl phenols, protein-based surfactants, quaternary surfactants, sarcosine derivatives, silicone-based surfactants, soaps, sorbitan derivatives, sucrose and glucose esters and derivatives, sulfates and sulfonates of oils and fatty acids, sulfates and sulfonates of ethoxylated alkyl phenols, sulfates of alcohols, sulfates of ethoxylated alcohols, sulfates of fatty esters, sulfonates of condensed naphthalenes, sulfonates of dodecyl and tridecyl benzene, sulfonates of petroleum, sulfosuccinamates and sulfosuccinates and their derivatives. Sulfonated amines and amides such as sodium N-methyl-N-oleoyl taurate (OMT) or potassium N-methyl-N-oleoyl taurate (KOMT) are particularly useful. Hydrophilic water-miscible polymeric stabilizers containing an anchoring group to the particle and a hydrophilic stabilizing group can also be used, such as those mentioned in Polymeric *Stabilization of Colloidal Dispersions* by D. H. Napper, Academic Press: New York; 1983, the contents of which are incorporated by reference.

The aqueous phase can further comprise one or more surfactants (other than the dispersing surfactants described above) colorants, block or graft copolymers, pharmaceutical agents, biocides, catalysts (besides those used to react with the inorganic gel precursors), metal oxide particles, organic or inorganic filler particles, or bioactive materials, all of which then become part of the porous particles. The amounts at which these addenda are included would be readily apparent to one skilled in the art and depend upon the intended use of the porous particles.

The aqueous phase can be neutralized by the addition of the one or more acids or bases described above. Conditions for neutralization include selecting a pH at which the gelation time of the aqueous phase is at least 5 and up to and including 60 minutes, and typically at least 10 and up to and including 30 minutes. One of ordinary skill in the art can determine the optimal pH to obtain a desirable gel time.

After neutralization, an oil-in-water emulsion is formed using the first oil phase and the aqueous phase. This oil-in-water emulsion comprises the organic microgel particles in the first oil phase, which is dispersed as first oil phase droplets in the aqueous phase. For example, the oil-in-water emulsion can be formed by emulsifying the first oil phase and the aqueous phase for example, using a high shear device. Any known emulsifying technique and conditions using any type of mixing and shearing equipment can be employed to make this oil-in-water emulsion. Such equipment includes but is not limited to, a batch mixer, planetary mixer, single or multiple screw extruder, dynamic or static mixer, colloid mill, high pressure homogenizer, sonicator, or a combination thereof. While any high shear type agitation device is useful, a particularly useful homogenizing device is the Microfluidizer® such as Model No. 110T produced by Microfluidics Manufacturing operating at >5000 psi (>352 kg/cm$^2$). In this device, the droplets of the first oil phase can be dispersed and reduced in size in the aqueous phase in a high flow agitation zone and, upon exiting this zone, the droplets of the first oil phase are reduced to a uniform size. The temperature of the emulsification can be modified to achieve the optimum viscosity for emulsification of the first oil phase droplets, and obtain the desired gel time of the aqueous phase.

A second oil phase is provided, which second oil phase comprises a second water-immiscible aprotic solvent having a dielectric constant of less than 10 and a dispersing surfactant. Useful water-immiscible aprotic solvents can be the same or different in the two oil phases and are described above. Thus, the first and second water-immiscible aprotic solvents can be selected from aliphatic and aromatic hydrocarbons, and a mixture of two or more of these aprotic solvents, as further defined above. In most instances, the first and second water-immiscible aprotic solvents are the same material or same mixtures of solvents.

The dispersing surfactant in the second oil phase is generally an oleophilic (oil-soluble or oil-miscible) surfactant having a hydrophilic head group such as a sorbitan, polyether, polyoxyethylene, sulfosuccinate, phosphate, carboxylate, sulfate, amino or acetylacetonate and a hydrophobic tail group, which can be a straight chain or branched. Examples include sorbitan esters (for example, sorbitan monooleate, monopalmitate, monostearate), sold under the trademark Span™, alkylarylpolyethers also called alkyl phenol ethoxylates, which are sold under the trademark Triton®, alcohol ethoxylates sold under the trademarks Brij® (polyoxyethylene alkyl ether) and Tween™ (polyoxyethylene sorbitan alkylate), sulfosuccinates sold under the trademark Aerosol™ and polyisobutylene succinimide sold under the trademark Oloa®. Oil-miscible polymeric stabilizers containing a hydrophilic anchoring group and an oleophilic stabilizing group can also be used, such as those mentioned in Polymeric Stabilization of Colloidal Dispersions by D. H. Napper, Academic Press: New York; 1983, the contents of which are incorporated by reference. Polymeric dispersants such as those sold under the trademark Solsperse® are particularly useful.

The oil-in-water emulsion described above is then combined with the second oil phase to form an oil-in-water-in-oil emulsion comprising the first oil phase droplets in the aqueous phase, which is dispersed as aqueous phase droplets in the second oil phase. This emulsifying process can be carried out using equipment and conditions described above for formation of the oil-in-water emulsion. Shear or extensional mixing or flow process can be controlled in order to minimize disruption of the distinct droplets in the mixture of various phases. Droplet size reduction can be achieved by homogenizing the oil-in-water-in-oil emulsion with a rotor stator mixer, through a capillary orifice device, or other suitable flow geometry. The shear field used to create the droplets can be obtained using standard shear geometries, such as an orifice plate or capillary. However, the flow field can also be generated using alternative geometries, such as packed beds of beads, or stacks or screens that impart an additional extensional component to the flow. It is well known in the literature that membrane-based emulsifiers can be used to generate multiple emulsions. The techniques allow the droplet size to be tailored across a wider range of sizes by adjusting the void volume or mesh size, and can be applied across a wide range of flow rates. The back pressure suitable for producing acceptable particle size and size distribution is at least 100 psi and up to and including 5000 psi (7 to 352 kg/cm$^2$, or typically at least 500 and up to and including 3000 psi (35.2 to 211 kg/cm$^2$). The flow rate is generally at least 1000 ml/min and up to and including 6000 ml/min particularly when a capillary orifice device is used.

Precursor inorganic porous particles are then formed by condensing the inorganic gel precursor in the aqueous phase droplets. This condensation is initiated by neutralization of the inorganic gel precursor in the aqueous phase in the first emulsion step so that the particles are gelled within 30 minutes of the second emulsification step. The condensation time is typically from 0 and up to and including 30 days but more typically at least 30 minutes and up to and including 12 hours and even more typically about 1 hour.

The precursor inorganic porous particles contain liquid in the first and second sets of pores, this liquid can be removed as the precursor inorganic porous particles are isolated to provide inorganic porous particles containing the first and second sets of pores. For example, the precursor inorganic porous particles can be isolated by separating the precursor inorganic porous particles from the second oil phase, washing, and drying. Thus, such isolation includes removal of the second water-immiscible aprotic solvents of the second oil phase by among other methods, filtration, centrifugation, or decantation to provide precursor porous particles that are then subjected to washing and drying the remaining solvents such as water in the mesopores, the aprotic first solvent in the macro pores and any residual second aprotic solvent, for example in an oven at 40° C. to provide the inorganic porous particles. The drying temperature can be at least −196° C. (in liquid nitrogen for freeze drying) and up to and including 300° C. for supercritical drying, but is more typically at least 20° C. and up to and including 80° C. The maximum temperature is dictated by the thermal stability of the active ingredients) encapsulated in the inorganic porous particles. Typically drying is carried out at a temperature in the range of at least 10° C. and up to and including 50° C., more typically at least 12° C. and up to and including 40° C. The drying time is typically at least 30 minutes and up to and including 30 days but more typically at least 1 day and up to and including 1 week.

Useful surface stabilizing agents include but are not limited to inorganic stabilizers such as clay particles, colloidal oxides (for example those sold under the trademarks Cab-O-Sil, Aerosil®, and Catapal®). Combinations of these surface stabilizing agents can also be used. The actual amount of surface stabilizing agent used in the method depends on the size of the final inorganic porous particles desired, which in turn depends upon the volume and weight ratios of the various phases used for making the multiple emulsions. While not intending to be limiting for this invention, the amount of surface stabilizing agent can be at least 0.1 weight % and up to and including 10 weight %, or typically at least 0.2 weight % and up to and including 5 weight %, based on the total weight of the oil-in-water-in-oil emulsion and depending upon the particle size of the surface stabilizing agent (for example, colloidal or fumed silica particles) and the size of the aqueous phase droplets.

The final size of the inorganic porous particles and the final size of the pores of the inorganic porous particles are governed by the balance between the capillary pressure of the pore fluid which causes shrinkage, and the modulus of the solid matrix of the particle during drying. The small pore radii can lead to large capillary pressures during drying as described by Laplace's equation:

$$\Delta P = 2\gamma(\cos\theta)/r$$

wherein $\Delta P$ is the pressure difference in the capillaries, $\gamma$ is the specific surface energy of the of the liquid-vapor interface, $\theta$ is the contact angle that the meniscus makes with the pore wall, and r is the pore radius. For a wetting fluid ($\theta<90°$), capillary pressure is negative, indicating that the fluid is in tension. When the pore fluid is removed as a vapor phase from the interconnected solid gel network under supercritical drying conditions, the network does not collapse and a low density aerogel is produced. However, if it is desired to dry the gel at or near ambient pressure by thermal evaporation, shrinkage will occur. When the sol-gel particles are produced from an oil-in-water-in oil emulsion, the presence of the organic microgel particles in the first emulsion prevent the collapse of the macropores greater than 100 nm in size during drying at or near ambient pressure.

The present invention provides at least the following embodiments and combinations thereof, but other combinations of features are considered to be within the present invention as a skilled artisan would appreciate from the teaching of this disclosure:

1. A method of making an inorganic porous particle comprising an inorganic compound that provides an inorganic solid phase including an external particle surface, and further comprising a first set of pores wherein the pores have an average diameter of less than 100 nm and a second set of pores wherein the pores have an average diameter of at least 100 nm, which second set of pores comprise stabilizing organic microgel particles, and the first and second sets of pores are isolated from each other in the inorganic solid phase, the method comprising:
providing a first oil phase comprising a first water-immiscible aprotic solvent having a dielectric constant of less than 10 and having dissolved therein organic microgel particles, providing an aqueous phase comprising a polar solvent, an inorganic gel precursor, a catalyst, and a dispersing surfactant, neutralizing the aqueous phase to initiate condensation of the inorganic gel precursor, providing an oil-in-water emulsion that comprises the organic microgel particles in the first oil phase, which is dispersed as first oil phase droplets in the aqueous phase, providing a second oil phase comprising a second water-immiscible aprotic solvent having a dielectric constant of less than 10 and a dispersing surfactant, combining the oil-in-water emulsion with the second oil phase to form an oil-in-water-in-oil emulsion comprising the first oil phase droplets in the aqueous phase, which is dispersed as aqueous phase droplets in the second oil phase, condensing the inorganic gel precursor in the aqueous phase droplets, and forming precursor inorganic porous particles wherein the inorganic porous particles contain a first set of pores wherein the pores have an average diameter less than 100 nm and a second set of pores wherein the pores have an average diameter of at least 100 nm.

2. The method of embodiment 1 further comprising isolating the inorganic porous particles from the precursor inorganic porous particles.

3. The method of embodiment 1 or 2 comprising isolating the inorganic porous particles by separating the precursor inorganic porous particles from the second oil phase, and washing and drying the precursor inorganic porous particles.

4. The method of any of embodiments 1 to 3 wherein the first and second water-immiscible aprotic solvents are different.

5. The method of any of embodiments 1 to 4 wherein the first and second water-immiscible aprotic solvents are selected from aliphatic and aromatic hydrocarbons, and a mixture of two or more of these aprotic solvents.

6. The method of any of embodiments 1 to 5 wherein the polar solvent in the aqueous phase is selected from the group consisting of water-miscible alcohols having 1 to 8 carbon atoms.

7. The method of any of embodiments 1 to 6 wherein the catalyst in the aqueous phase is an inorganic or organic acid or an inorganic or organic base.

8. The method of any of embodiments 1 to 7 wherein the neutralizing of the aqueous phase is carried out to obtain a gel time of the aqueous phase of at least 5 and up to and including 60 minutes.

9. The method of any of embodiments 1 to 8 wherein the first oil phase further comprises an organic polymer dispersant that is more soluble in the first oil phase than in the aqueous phase.

10. The method of any of embodiments 1 to 9 wherein the dispersing surfactant in the aqueous phase further is a hydrophilic surfactant.

11. The method of any of embodiments 1 to 10 wherein the dispersing surfactant in the second oil phase is an oleophilic surfactant.

12. The method of any of embodiments 1 to 11 wherein each organic microgel particle comprises a copolymer that comprises randomly recurring units from each of a) and b) below:

a) recurring units derived from crosslinkable ethylenically unsaturated polymerizable monomers, and b) recurring units derived from one or more of:
i) an ethylenically unsaturated polymerizable monomer, the homopolymer of which would be insoluble in but swellable by an isoparaffinic hydrocarbon liquid,
ii) an ethylenically unsaturated polymerizable monomer, the homopolymer of which would be soluble in the isoparaffinic hydrocarbon liquid, and iii) an ethylenically unsaturated polymerizable monomer, the homopolymer of which would be insoluble in and not swellable by the isoparaffinic hydrocarbon liquid.

13. The method of embodiment 12 wherein each organic microgel particle comprises recurring units derived from a mixture of ethylenically unsaturated polymerizable monomers, wherein at least 0.5 and up to and including 15 weight % of the mixture of monomers comprises a) monomers, and the remainder of the mixture of monomers comprises b) monomers.

14. The method of any of embodiments 1 to 13 wherein the oil-in-water emulsion is provided by emulsifying the first oil phase and the aqueous phase using a high shear device.

15. The method of any of embodiments 1 to 14 wherein the inorganic gel precursor comprises a substituted or unsubstituted alkoxide.

16. The method of any of embodiments 1 to 15 wherein the inorganic gel precursor comprises a substituted alkoxide having one or more alkyl, aryl, aminoalkyl, aminoaryl, glycidoxyalkyl, or glycidoxyaryl substituents, or a mixture thereof.

17. The method of any of embodiments 1 to 16 wherein the aqueous phase further comprises one or more surfactants, colorants, block or graft copolymers, metal oxide particles, organic or inorganic filler particles, or bioactive materials.

18. The method of any of embodiments 1 to 17 wherein the second set of pores in the inorganic porous particle is at least partially filled with the organic microgel particles.

19. The method of any of embodiments 1 to 18 wherein the average diameter of the pores in the first set of pores in the inorganic porous particle is at least 1 nm but less than 100 nm and the average diameter of the pores in the second set of pores is at least 100 nm and up to and including 10,000 nm, and the inorganic porous particle has an average diameter of at least 1 µm and up to and including 100 µm.

20. The method of any of embodiments 1 to 19 wherein the inorganic porous particle has a porosity of at least 10% and up to and including 70%.

21. The method of any of embodiments 1 to 20 wherein less than 20% of the volume of the second set of pores comprises the stabilizing organic microgel particles.

The following Examples are provided to illustrate the practice of this invention and are not meant to be limiting in any manner.

Preparation of Hydrolyzed Silane Solution 1:

A hydrolyzed silane solution was prepared by combining 43.15 weight % of tetramethoxysilane (Sigma Aldrich), 36.41 weight % of methanol, and 20.44 weight % of 0.15N hydrochloric acid in a glass jar. This solution was mixed on a roller mill for 24 hours at ambient temperature.

All average (arithmetic mean) porous particle sizes were determined by optical transmission microscopy.

Comparative Example 1

A preparation of inorganic porous particles without stabilized organic microgel particles in the first oil phase was carried out as follows:

An aqueous phase was prepared by combining 25.0 g of hydrolyzed silane Solution 1 with 2.5 g of a 10 weight % solution of potassium methyl oleoyl taurate dispersant and was adjusted to pH 4.7+/−0.2 with 0.1N sodium hydroxide. A first oil-in-water emulsion was prepared by dispersing 2.5 g of cyclohexane in the aqueous phase by sonication using a Cole Palmer 4710 Ultrasonic Homogenizer probe at 70% duty cycle for 40 seconds.

An oil-in-water-in oil emulsion ("second emulsion") was prepared by dispersing the first oil-in-water emulsion in 225 g of a solution of 6 weight % of Span® 60 sorbitan monostearate dispersant (Croda, Inc.) in cyclohexane using a Silverson rotor-stator mixer at 5000 rev/min for 1 minute. This oil-in-water-in-oil emulsion was then stirred for 30 minutes to gel the resulting particles. After stirring, the resulting particles were allowed to settle, the cyclohexane was decanted off, and the particles were rinsed twice with ethanol to remove excess surfactant and dried in a vacuum oven overnight at ambient temperature. The dried particles were sieved though a 100-nm mesh screen to remove clumps. The mesopore size and pore size distribution of the dried particles was measured after degassing overnight at 120° C. by nitrogen gas adsorption using a NOVA Model 3000 surface area and pore size analyzer (Quantachrome Instruments). The macropore size distribution was measured by visual examination of particle cross-section images taken using a scanning electron microscope. The macropores were measured by obtaining cross sections and their examination by scanning electron microscopy. This procedure involved spreading the dried porous particles on a polyester support, adding 5 drops of a rapidly drying cement, mixing the cement and particles, and allowing the mixture dry for 4 hours. A sample of the support with the dried mixture was then placed in the chuck of a microtome and the face of the sample was sliced off with the microtome. A section of the sliced sample was placed in vice-like stub holder for microscopic analysis. The sliced sample was then examined with a 5 kv Hitachi 4000 FEG Scanning Electron Microscope. The macropore size was determined by visual inspection of images of the sliced sample. The average inorganic porous particle size was 5.4 µm.

Invention Example 1

Inorganic porous particles were prepared using weakly cationic stabilizing organic microgel particles in the first oil phase. The inorganic porous particles were prepared in the same manner as described in Comparative Example 1 except that the first oil phase contained 10 weight % of organic microgel particles composed of poly(isobutyl methacrylate-co-2-ethyl hexyl methacrylate-co-divinyl benzene-co-N-[2-(methacryloyloxy)ethyl]-N,N,N,trimethylammonium methosulfate) (71.75/25/3/0.25 weight ratio) and 1 weight % of Oloa® 11000 polyisobutylene succinimide dispersant (Chevron Oronite) in cyclohexane. The average inorganic porous particle size was 92 µm.

Invention Example 2

Inorganic porous particles were prepared using weakly anionic stabilizing organic microgel particles in the first oil phase. The inorganic porous particles were prepared in the same manner as described in Invention Example 2 except that the first oil phase contained 10 weight % of organic microgel particles composed of poly(isobutyl methacrylate-co-2-ethyl hexyl methacrylate-co-divinyl benzene-co-methacrylic acid) (71.75/25/3/0.5 weight ratio). The mean inorganic porous particle size, before drying, as measured by light scattering with a Horiba LA-920 analyzer, was 24.1 µm. The average inorganic porous particle size was 7.5 µm.

Invention Example 3

Inorganic porous particles were prepared using nonionic stabilizing organic microgel particles in the first oil phase. The inorganic porous particles were prepared in the same manner as described in Invention Example 2 except that the first oil phase contained 10 weight % of organic microgel particles composed of poly(isobutyl methacrylate-co-2-ethyl hexyl methacrylate-co-divinyl benzene) (82/15/3 weight ratio). The mean inorganic porous particle size, before drying, as measured by light scattering with a Horiba LA-920 analyzer, was 21.1 µm. The average inorganic porous particle size was 3.8 µm.

Invention Example 4

Inorganic porous particles were prepared using nonionic stabilizing organic microgel particles in the first oil phase. The inorganic porous particles were prepared in the same manner as described in Invention Example 2 except that the first oil phase contained 2 weight % of organic microgel particles composed of poly(2-ethyl hexyl methacrylate-co-p-t-butyl styrene-co-divinyl benzene) (50/47/3 weight ratio) and the second oil phase was a solution of 2.1 weight % of Span® 60 sorbitan monostearate, 0.7 weight % of Span® 80 sorbitan monooleate (Sigma Aldrich), and 2.8 weight % of Solsperse® 28000 (Lubrizol Corp) in cyclohexane. The mean inorganic porous particle size, before drying, as measured by light scattering with a Horiba LA-920 analyzer, was 50 µm. The average inorganic porous particle size was 11.1 µm.

Invention Example 5

Inorganic porous particles were prepared using nonionic stabilizing organic microgel particles in the first oil phase. The inorganic porous particles were prepared in the same manner as described in Invention Example 4 except that the first oil phase contained 5 weight % of organic microgel particles composed of poly(2-ethyl hexyl methacrylate-co-p-t-butyl styrene-co-divinyl benzene) (50/47/3 weight ratio). The mean inorganic porous particle size, before drying, as measured by light scattering with a Horiba LA-920 analyzer, was 25 µm. The average inorganic porous particle size was 6.7 µm.

Invention Example 6

Inorganic porous particles were prepared using nonionic stabilizing organic microgel particles in the first oil phase. The inorganic porous particles were prepared in the same manner as described in Invention Example 4 except that the first oil phase contained 10 weight % of organic microgel particles composed of poly(2-ethyl hexyl methacrylate-co-p-t-butyl styrene-co-divinyl benzene) (50/47/3 weight ratio). The mean inorganic porous particle size, before drying, as measured by light scattering with a Horiba LA-920 analyzer, was 40 µm. The average inorganic porous particle size was 6 µm.

A summary of the inorganic porous particles for Comparative Example 1 and Invention Examples 1-6 is provided below in TABLE I. These results show that the presence of organic microgels in the first emulsion yields inorganic porous particles according to this invention having a stable pore hierarchy of two distinct sets of pores, one set being mesopores and the second set being macropores.

TABLE I

| Example | Organic microgel in first oil phase | Organic microgel level in first oil phase | Average mesopore diameter (nm) | Macropore appearance (photos attached) |
|---|---|---|---|---|
| Comparative | None | None | 4.0 | Very few or no visible macropores |
| Invention 1 | Poly(isobutyl methacrylate-co-2-ethyl hexyl methacrylate-co-divinyl benzene-co-N-[2-(methacryloyloxy)ethyl]-N,N,N,trimethylammonium methosulfate) (71.75/25/3/0.25) | 10% | 3.2 | Many pores over 0.1 µm in diameter |
| Invention 2 | Poly(isobutyl methacrylate-co-2-ethyl hexyl methacrylate-co-divinyl benzene-co-N-[2-(methacryloyloxy)ethyl]) | 10% | 4.3 | Many pores over 0.1 µm in diameter |
| Invention 3 | Poly(isobutyl methacrylate-co-2-ethyl hexyl methacrylate-co-divinyl benzene) (82/15/3) | 10% | 4.8 | Many pores over 0.1 µm in diameter |
| Invention 4 | Poly(2-ethyl hexyl methacrylate-co-p-t-butyl styrene-co-divinyl benzene) (50/47/3) | 2% | 6.0 | Many pores over 0.1 µm in diameter |
| Invention 5 | Poly(2-ethyl hexyl methacrylate-co-p-t-butyl styrene-co-divinyl benzene) (50/47/3) | 5% | 5.7 | Many pores over 0.1 µm in diameter |
| Invention 6 | Poly(2-ethyl hexyl methacrylate-co-p-t-butyl styrene-co-divinyl benzene) (50/47/3) | 10% | 5.9 | Many pores over 0.1 µm in diameter |

The invention has been described in detail with particular reference to certain preferred embodiments thereof, but it will be understood that variations and modifications can be effected within the spirit and scope of the invention.

The invention claimed is:

1. A method of making an inorganic porous particle comprising an inorganic compound that provides an inorganic solid phase including an external particle surface, and further comprising a first set of pores wherein the pores have an average diameter of less than 100 nm and a second set of pores wherein the pores have an average diameter of at least 100 nm, which second set of pores comprise stabilizing organic microgel particles, and the first and second sets of pores are isolated from each other in the inorganic solid phase, the method comprising:
providing a first oil phase comprising a first water-immiscible aprotic solvent having a dielectric constant of less than 10 and having dissolved therein organic microgel particles,
providing an aqueous phase comprising a polar solvent, an inorganic gel precursor, a catalyst, and a dispersing surfactant,
neutralizing the aqueous phase to initiate condensation of the inorganic gel precursor,
providing an oil-in-water emulsion that comprises the organic microgel particles in the first oil phase, which is dispersed as first oil phase droplets in the aqueous phase,
providing a second oil phase comprising a second water-immiscible aprotic solvent having a dielectric constant of less than 10 and a dispersing surfactant,
combining the oil-in-water emulsion with the second oil phase to form an oil-in-water-in-oil emulsion comprising the first oil phase droplets in the aqueous phase, which is dispersed as aqueous phase droplets in the second oil phase,
condensing the inorganic gel precursor in the aqueous phase droplets, and
forming precursor inorganic porous particles wherein the inorganic porous particles contain a first set of pores wherein the pores have an average diameter less than 100 nm and a second set of pores wherein the pores have an average diameter of at least 100 nm.

2. The method of claim 1 further comprising isolating the inorganic porous particles from the precursor inorganic porous particles.

3. The method of claim 2 comprising isolating the inorganic porous particles by separating the precursor inorganic porous particles from the second oil phase, and washing and drying the precursor inorganic porous particles.

4. The method of claim 1 wherein the first and second water-immiscible aprotic solvents are different.

5. The method of claim 1 wherein the first and second water-immiscible aprotic solvents are selected from aliphatic and aromatic hydrocarbons, and a mixture of two or more of these aprotic solvents.

6. The method of claim 1 wherein the polar solvent in the aqueous phase is selected from the group consisting of water-miscible alcohols having 1 to 8 carbon atoms.

7. The method of claim 1 wherein the catalyst in the aqueous phase is an inorganic or organic acid or an inorganic or organic base.

8. The method of claim 1 wherein the neutralizing of the aqueous phase is carried out to obtain a gel time of the aqueous phase for at least 5 and up to and including 60 minutes.

9. The method of claim 1 wherein the first oil phase further comprises an organic polymer dispersant that is more soluble in the first oil phase than in the aqueous phase.

10. The method of claim 1 wherein the dispersing surfactant in the aqueous phase further is a hydrophilic surfactant.

11. The method of claim 1 wherein the dispersing surfactant in the second oil phase is an oleophilic surfactant.

12. The method of claim 1 wherein each organic microgel particle comprises a copolymer that comprises randomly recurring units from each of a) and b) below:
a) recurring units derived from crosslinkable ethylenically unsaturated polymerizable monomers, and
b) recurring units derived from one or more of:
i) an ethylenically unsaturated polymerizable monomer, the homopolymer of which would be insoluble in but swellable by an isoparaffinic hydrocarbon liquid,
ii) an ethylenically unsaturated polymerizable monomer, the homopolymer of which would be soluble in the isoparaffinic hydrocarbon liquid, and
iii) an ethylenically unsaturated polymerizable monomer, the homopolymer of which would be insoluble in and not swellable by the isoparaffinic hydrocarbon liquid.

13. The method of claim 12 wherein each organic microgel particle comprises recurring units derived from a mixture of ethylenically unsaturated polymerizable monomers, wherein at least 0.5 and up to and including 15 weight % of the mixture of monomers comprises a) monomers, and the remainder of the mixture of monomers comprises b) monomers.

14. The method of claim 1 wherein the oil-in-water emulsion is provided by emulsifying the first oil phase and the aqueous phase using a high shear device.

15. The method of claim 1 wherein the inorganic gel precursor comprises a substituted or unsubstituted alkoxide.

16. The method of claim 1 wherein the inorganic gel precursor comprises a substituted alkoxide having one or more alkyl, aryl, aminoalkyl, aminoaryl, glycidoxyalkyl, or glycidoxyaryl substituents, or a mixture thereof.

17. The method of claim 1 wherein the aqueous phase further comprises one or more surfactants, colorants, block or graft copolymers, metal oxide particles, organic or inorganic filler particles, or bioactive materials.

18. The method of claim 1 wherein the inorganic porous particle comprises a pharmaceutical agent, biocide, chemical catalyst, dispersant, colorant, block or graft copolymer, metal oxide particles, organic or inorganic filler particles, or bioactive material.

19. The method of claim 1 wherein the second set of pores in the inorganic porous particle is at least partially filled with the organic microgel particles.

20. The method of claim 1 wherein the average diameter of the pores in the first set of pores in the inorganic porous particle is at least 1 nm but less than 100 nm and the average diameter of the pores in the second set of pores is at least 100 nm and up to and including 10,000 nm, and the inorganic porous particle has an average diameter of at least 1 μm and up to and including 100 μm.

21. The method of claim 1 wherein the inorganic porous particle has a porosity of at least 10% and up to and including 70%.

22. The method of claim 1 wherein less than 20% of the volume of the second set of pores comprises the stabilizing organic microgel particles.

* * * * *